(12) United States Patent
Baker

(10) Patent No.: US 7,371,221 B1
(45) Date of Patent: May 13, 2008

(54) CERVICAL BRACE AND THERAPY DEVICE

(76) Inventor: Ford S. Baker, 6161 Perkins Rd., Suite 2C, Baton Rouge, LA (US) 70808

(*) Notice: Subject to any disclaimer, the term of this patent is extended or adjusted under 35 U.S.C. 154(b) by 124 days.

(21) Appl. No.: 10/915,183

(22) Filed: Aug. 10, 2004

(51) Int. Cl.
*A61F 5/00* (2006.01)

(52) U.S. Cl. ............................................. 602/18

(58) Field of Classification Search ............ 602/17–19, 602/5, 32–40; 128/DIG. 23, 869, DIG. 19; 606/130; 2/421–422, 410, 425
See application file for complete search history.

(56) References Cited

U.S. PATENT DOCUMENTS

| | | | | |
|---|---|---|---|---|
| 2,474,200 A | * | 6/1949 | McBee | 602/18 |
| 2,820,455 A | * | 1/1958 | Hall | 602/18 |
| 3,477,425 A | * | 11/1969 | Grassl | 602/18 |
| 3,724,452 A | | 4/1973 | Nitschke | |
| 4,204,529 A | | 5/1980 | Cochrane | |
| 4,520,801 A | * | 6/1985 | Lerman | 602/18 |
| 4,582,051 A | * | 4/1986 | Greene et al. | 602/18 |
| 4,708,129 A | * | 11/1987 | Pujals, Jr. | 602/18 |
| 4,712,540 A | | 12/1987 | Tucker et al. | |
| 4,825,476 A | * | 5/1989 | Andrews | 2/461 |
| 4,886,052 A | * | 12/1989 | Calabrese | 602/18 |
| 4,953,856 A | * | 9/1990 | Fox, III | 482/105 |
| 4,988,093 A | | 1/1991 | Forrest et al. | |
| 5,005,563 A | * | 4/1991 | Veale | 602/18 |
| 5,040,547 A | * | 8/1991 | Bergstrom | 128/857 |
| 5,046,490 A | * | 9/1991 | Young et al. | 602/17 |
| 5,097,824 A | * | 3/1992 | Garth | 602/18 |
| 5,116,359 A | * | 5/1992 | Moore | 606/241 |
| 5,201,702 A | * | 4/1993 | Mars | 602/17 |
| 5,320,640 A | | 6/1994 | Riddle et al. | |
| 5,336,138 A | | 8/1994 | Arjawat | |
| 5,360,383 A | | 11/1994 | Boren | |
| 5,385,535 A | * | 1/1995 | McGuinness | 602/18 |
| 5,444,870 A | * | 8/1995 | Pinsen | 2/461 |
| 5,531,669 A | | 7/1996 | Varnau | |
| 5,546,601 A | * | 8/1996 | Abeyta | 2/468 |
| 5,575,763 A | | 11/1996 | Nagata et al. | |
| 5,855,582 A | * | 1/1999 | Gildenberg | 606/130 |
| 5,930,843 A | * | 8/1999 | Kelly | 2/468 |
| 5,964,722 A | * | 10/1999 | Goralnik et al. | 602/18 |
| 5,984,836 A | | 11/1999 | Casali | |
| 5,997,440 A | | 12/1999 | Hanoun | |
| 6,058,517 A | * | 5/2000 | Hartunian | 2/468 |
| 6,106,437 A | | 8/2000 | Brooks | |
| 6,210,354 B1 | * | 4/2001 | Ousdal | 602/36 |

(Continued)

*Primary Examiner*—Patricia Bianco
*Assistant Examiner*—Huong Q. Pham
(74) *Attorney, Agent, or Firm*—Roy, Kiesel, et al

(57) ABSTRACT

A cervical brace and therapy device for use to rehabilitate an injured neck of a person is described having a base support structure shaped to fit about the neck and rest on the shoulders of the person; a support ring assembly attachable to the base support structure in a horizontal position below the mandible of the person, the support ring assembly having an anterior section and a posterior section; a rotational member attached to the support ring assembly in a manner to rotate about the support ring assembly; and an occipital-mandible support member shaped to accommodate the mandible and the occipital portions of the head of the person, the occipital-mandible support member being attachable to the rotational member in a manner to permit the occipital-mandible support member a predetermined range of rotation.

26 Claims, 6 Drawing Sheets

U.S. PATENT DOCUMENTS

| | | | |
|---|---|---|---|
| 6,253,389 B1 * | 7/2001 | Scaglione | 2/456 |
| 6,267,741 B1 * | 7/2001 | Lerman | 602/18 |
| 6,458,090 B1 * | 10/2002 | Walpin | 602/18 |
| 6,551,214 B1 | 4/2003 | Taimela | |
| 6,599,257 B2 | 7/2003 | Al-Obaidi et al. | |
| 6,692,451 B2 | 2/2004 | Splane, Jr. | |
| 6,854,134 B2 * | 2/2005 | Cleveland | 2/422 |

* cited by examiner

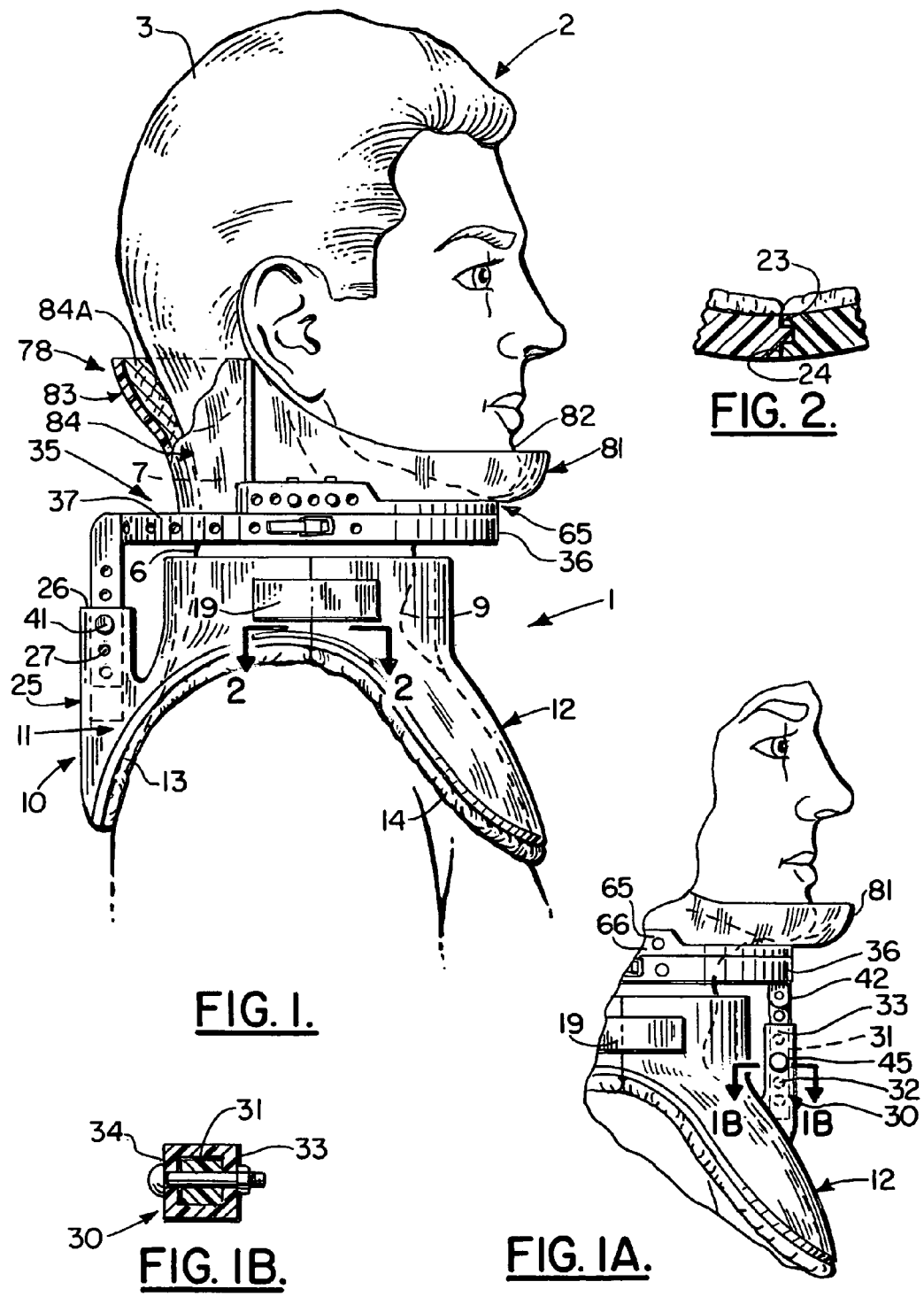

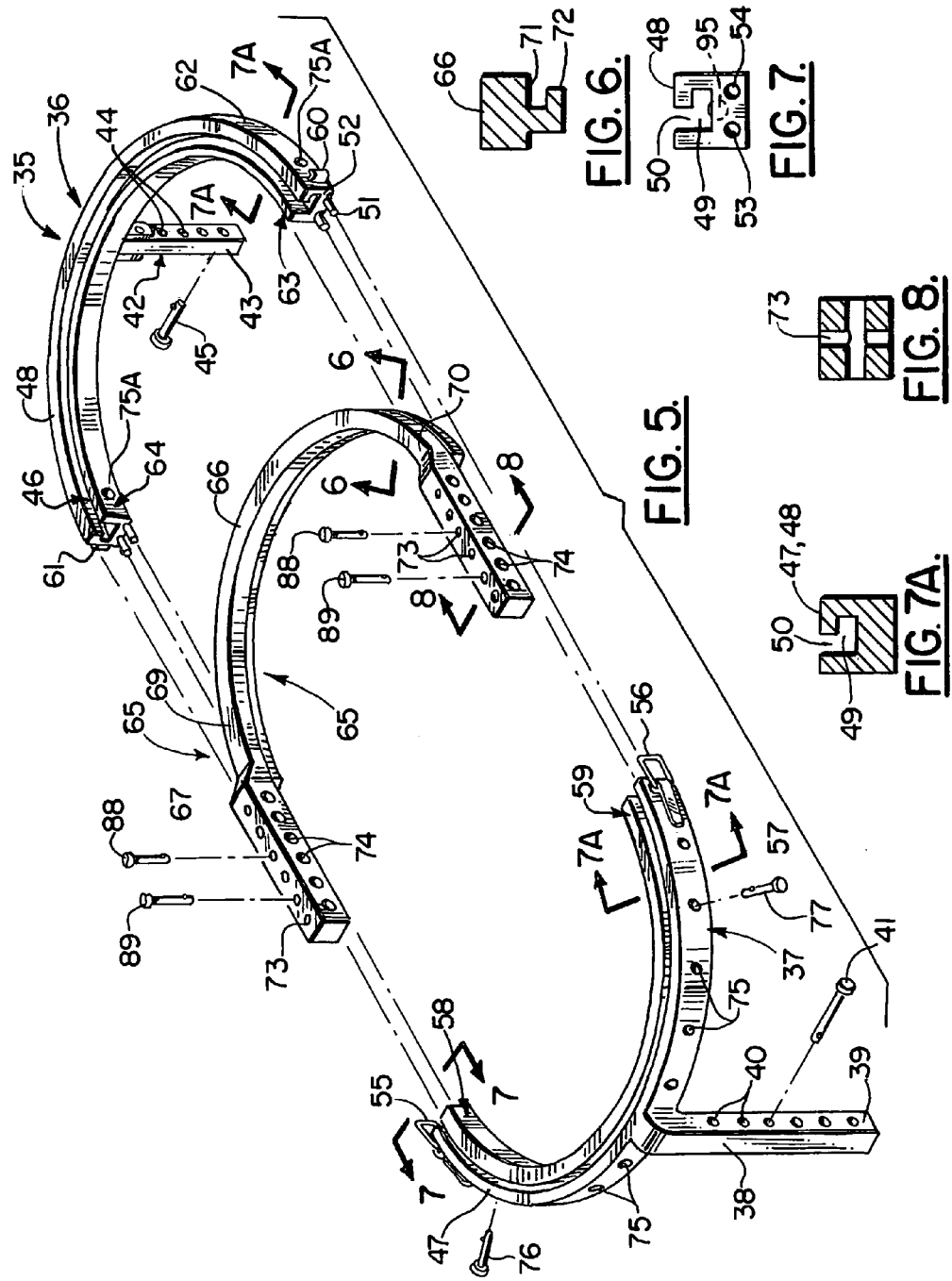

CERVICAL BRACE AND THERAPY DEVICE

FIELD OF THE INVENTION

The present invention pertains to the field of orthopedic devices, and more particularly to cervical brace and therapy devices for the head and neck.

BACKGROUND FOR THE INVENTION

Safely supporting the head and strengthening muscles of the neck following cervical spine or cervical-thoracic spine injuries is a delicate rehabilitative process. The anatomical region involved includes the occipital-cervical junction, cervicothoracic junction, cervical vertebrae, the upper thoracic vertebrae and all of the associated muscles, ligaments, tendons and other connective tissues in these regions.

The prior art includes numerous cervical orthoses designed to partially or totally immobilize the head and neck. Examples of such orthoses are described in U.S. Pat. No. 4,204,529 to Crochrane; U.S. Pat. No. 4,520,801 to Lerman; U.S. Pat. No. 4,712,540 to Tucker; U.S. Pat. No. 5,097,824 to Garth; U.S. Pat. No. 5,575,763 to Nagata et al. The immobilization provided by these devices result in a desired spinal alignment, reduced neck muscle strain or spasm and transfer the load of the head to the shoulder area. However, these cervical orthoses create the problem of extended immobilization weakening the muscles that stabilize the head and neck. They do not permit the rotation of the head which may result in further injury to the patient.

Another example of the prior art is illustrated in U.S. Pat. No. 6,458,090 to Walpin. The multi-positional support device disclosed allows for support in various fixed degrees of rotation as well as small ranges of head and neck rotation. However, this device presents the problem of small ranges of head and neck rotation insufficiently exercising atrophied neck muscles to strengthen them to safely support the load of the head and allow extensive ranges of rotation of the head.

Other known cervical therapy devices, such as described in U.S. Pat. No. 5,116,359 to Moore; U.S. Pat. No. 5,320,640 to Riddle et al; U.S. Pat. No. 5,336,138 to Arijawat; U.S. Pat. No. 6,551,214 to Taimela; U.S. Pat. No. 6,599,257 to Al-Obaidi et al; and U.S. Pat. No. 6,692,451 to Splane, support the head and therapeutically exercise the neck in one or more planes. However, these cervical therapy devices are cumbersome cervical therapy devices built onto a chair or table requiring patients to visit a physical therapy facility for cervical therapy.

Known neck exercise devices such as described in U.S. Pat. No. 4,988,093 to Forrest et al; U.S. Pat. No. 5,360,383 to Boren; U.S. Pat. No. 5,984,836 to Casali; U.S. Pat. No. 5,997,440 to Hanoun; and U.S. Pat. No. 6,106,437 to Brooks, usually include a head harness or helmet of various types and resistive forces. Such exercise devices are designed to strengthen neck muscles without supporting the cervical spine and without transferring the load of the head to the shoulders. This lack of support, load transfer and use of resistive forces risk injury to patients with muscles atrophied from immobilization and insufficient strength to safely support and rotate the head against resistive forces.

Therefore, one object of this invention is to provide an adjustable device wearable during the activities of daily living that comfortably supports the cervical and upper thoracic spine. Those learned in the art recognize the importance of strengthening atrophied neck muscles in one plane of motion at a time thus reducing the risk of injury to patients.

Another object of this invention is to provide a support and therapy device that comfortably transfers the load of the head to the shoulders and upper chest of the patient.

Still another object of this invention is to provide a support and therapy device that allows the neck muscles to strengthen with successive extensive ranges of active rotation in the horizontal plane without tilting the head.

A further object of this invention is to provide a wearable, adjustable cervical orthosis that facilitates a method of cervical therapy where the head actively rotates in successive extensive ranges of horizontal rotation without tilting.

A still further object of this invention is to provide a support and therapy device having support and therapy functions that safely strengthen muscles responsible for head rotation that have atrophied by immobilization in known cervical support devices or as a result of neuromuscular disease thus permitting safe increases in the range of head rotation during treatment.

Another object of this invention is to provide a cost effective support and therapy device.

These and other objects and advantages of this invention shall become apparent from the ensuing descriptions of the invention.

SUMMARY OF THE INVENTION

The cervical brace and therapy device for use to rehabilitate an injured neck of a person is constructed having a base support structure shaped to fit about the neck and rest on the shoulders of the person. Attachable to the base support structure is a support ring assembly. The support ring assembly is attached to be in a horizontal position below the mandible of the person. Attached to the support ring assembly is a rotational member. The attachment is done in a manner to permit the rotational member to rotate about the support ring assembly in a predetermined range of horizontal rotation. In addition there is an occipital-mandible support member shaped to accommodate the mandible and the occipital portions of the head of the person. The occipital-mandible support member being attachable to the rotational member in a manner to permit the occipital-mandible support member to rotate up to the predetermined range of horizontal rotation.

BRIEF DESCRIPTION OF THE DRAWINGS

FIG. 1 is a side view of one preferred embodiment of the cervical brace and cervical therapy device positioned on the patient.

FIG. 1A is a partial side view of an alternative embodiment similar to FIG. 1, but wherein an anterior support strut is utilized to better maintain the support ring assembly in a horizontal position.

FIG. 1B is a cross-sectional view taken along lines 1B-1B of FIG. 1A.

FIG. 2 is a cross-sectional view taken along lines 2-2 of FIG. 1.

FIG. 5 is an exploded view illustrating the connectivity of the anterior and posterior support ring assembly members with the arcuate rotational member of the preferred embodiment of FIG. 1.

FIG. 6 is an end view taken along lines 6-6 of FIG. 5.

FIG. 7 is a cross-sectional view taken along lines 7-7 of FIG. 5.

FIG. 7A is a cross-sectional view taken along lines 7-7 of FIG. 5.

FIG. 8 is a cross-sectional view taken along lines 8-8 of FIG. 5.

DETAILED DESCRIPTION OF THE INVENTION

Figure 3:
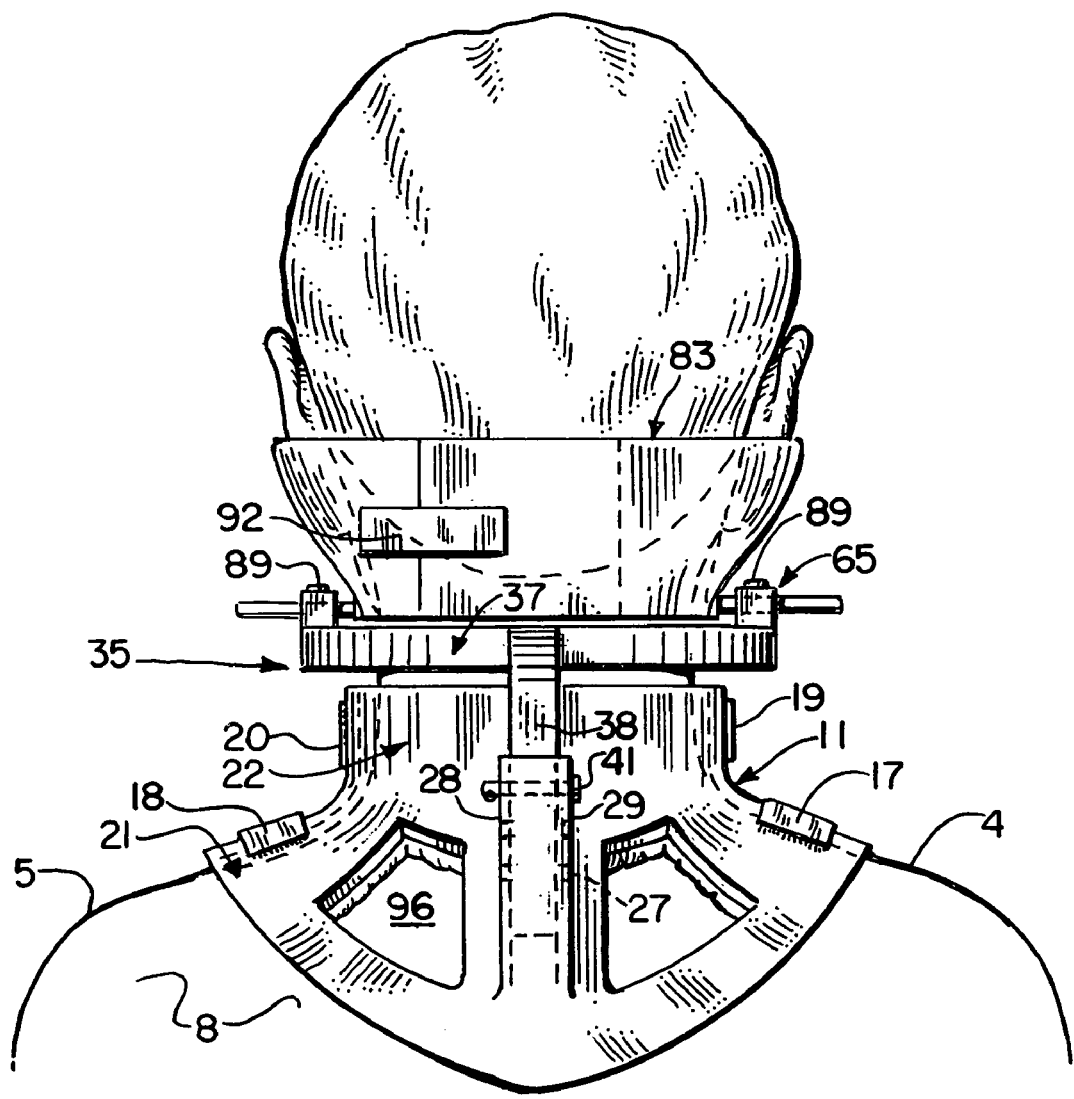
FIG. 3 is a back view of the preferred embodiment of FIG. 1 positioned on the patient.

Without attempting to limit the scope of the invention, the preferred embodiments of the invention are described with reference to FIGS. 1-10.

As seen in FIGS. 1-4, the cervical brace and therapy device 1 is positioned for use on the patient 2 being treated for a neck injury. The device 1 comprises four basic elements: a base support structure 10, a support ring assembly 35, a rotational member 65 and an occipital-mandible support member 78.

The function of the base support structure 10 is to provide a stable platform for transferring the load or weight of the patient head 3 principally to the patient left and right shoulders 4 and 5, respectively, and to a lesser extent to the back side 6 of the patient neck 7, the patient upper back 8, and the patient sternum area 9. In one of its preferred embodiments base support structure 10 include a rear neck contoured plate 11 and a front neck-sternum plate 12. Both plates 11 and 12 are molded from a thermoset plastic or resin and shaped to conform generally to rest on shoulders 4 and 5, patient back side 6 of the neck and patient upper back 8. Each plate is also provided with a cushioning pad 13 and 14, respectively, that is attached to the interior surface walls 15 and 16, respectively, to provide cushioning of the load on shoulders 4 and 5. Once plates 11 and 12 are positioned on the shoulders 4 and 5, respectively, they are attached to one another by fastening means 17, 18, 19 and 20 located on the shoulder section 21 and neck section 22 of plates 11 and 12, respectively. A preferred fastening means is a conventional hook and loop fastener; although other known fasteners such as latch assemblies, snaps, cinches or combinations of these can be used.

Figure 4:
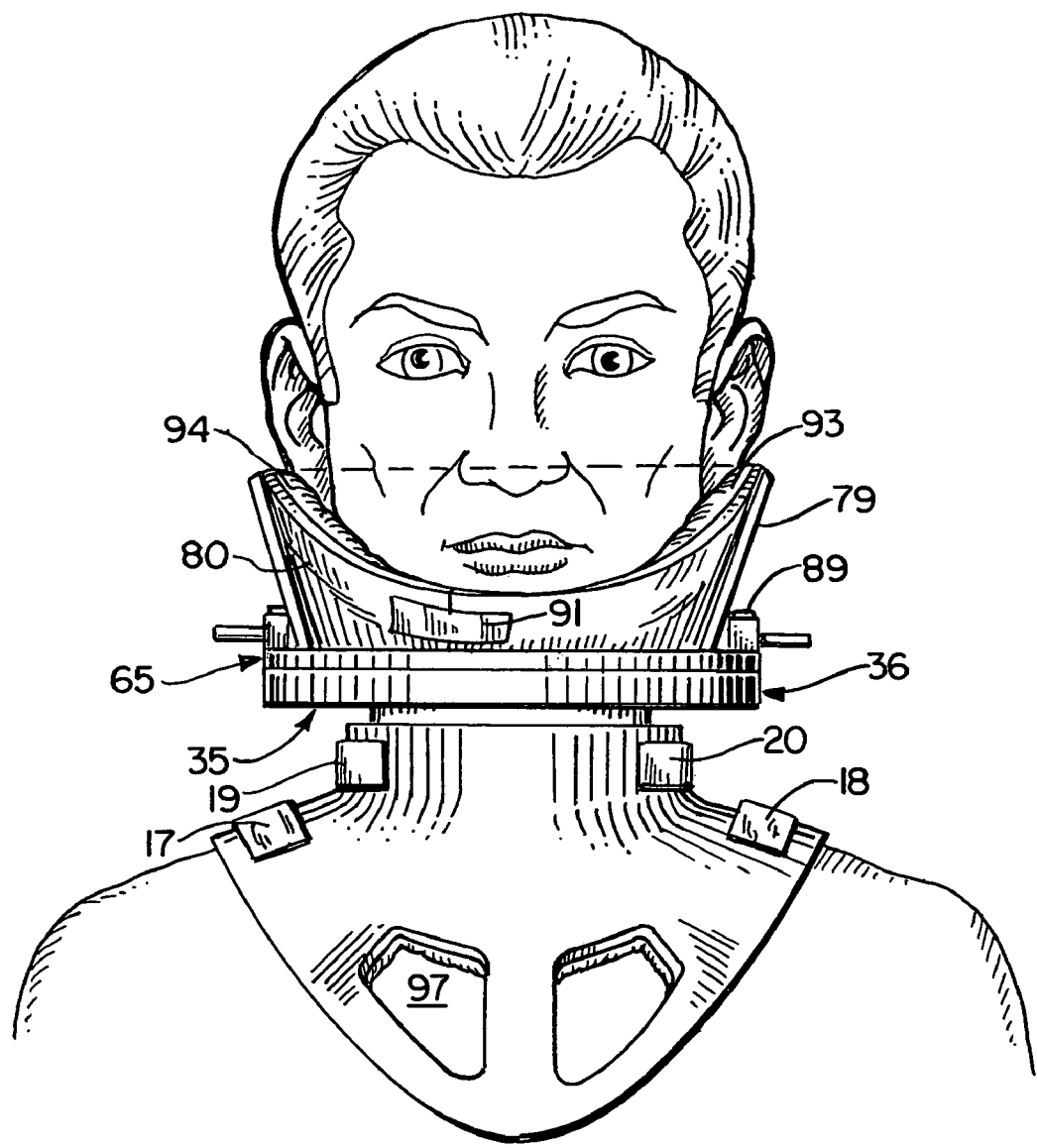
FIG. 4 is a front view of the preferred embodiment of FIG. 1 positioned on the patient.

As illustrated in FIG. 2, in a preferred embodiment the abutting edges 23 and 24 of plates 11 and 12 are constructed in a mating tongue-and-groove design to facilitate alignment of the two plates, as well provide for a more stable platform for the load or weight transfer from the head 3 to the shoulders 4 and 5. Other known interlocking or overlapping joint designs can be employed. In another preferred embodiment as illustrated in FIGS. 3 and 4, plates 11 and 12 do not need to be solid, but can be constructed having open areas 96 and 97, respectively, to reduce their weight, better ventilate the body heat, and increase wearing comfort.

Plate 11 is provided with a vertically extending tubular member 25 constructed from a hard plastic or other similar material to provide rigidity to the member. Tubular member 25 is constructed having a central cavity 26. A series of aligned openings 27 are provided in the opposite side walls 28 and 29 of tubular member 25 to position support ring assembly 35 in its desired position as discussed below.

In a more preferred embodiment illustrated in FIG. 1A and FIG. 1B, plate 12 is provided with a vertically extending tubular member 30 also constructed from a hard plastic or other similar material to provide rigidity to the member. The tubular member 30 is constructed having a tubular central cavity 31. A series of aligned openings 32 are provided in the opposite side walls 33 and 34 of tubular member 30. In this embodiment support ring assembly 35 will be more securely held in the desired horizontal position and be more able to prevent the patient head from tilting which may cause further injury to the neck.

Referring now to FIGS. 4-8 a preferred embodiment of support ring assembly 35 and rotational member 65 are illustrated. Support ring assembly 35 comprises an anterior section 36 and a posterior section 37. In a preferred embodiment anterior section 36 and posterior section 37 will form a circle when joined together. The posterior section 37 is provided with a vertically downwardly extending bar 38 having a cross-section similar in shape but slightly smaller than the cross-section of central cavity 26 to permit the lower end 39 of bar 38 to be positioned in central cavity 26. Bar 38 is provided with a series of vertically aligned openings 40 extending through bar 38. The height of support ring assembly 35 can be adjusted by moving bar 38 vertically up and down in central cavity and fixed at the desired height by inserting a locking pin 41 through one pair of aligned openings 27 and one of openings 40 (see also FIG. 1). The locking pin 41 can be selected from any number of well known structures that can be used to secure the alignment. Examples include cotter pins, bolts, screws (if the openings are threaded), etc.

In a preferred embodiment the anterior section 36 is also provided with a vertically downward extending bar 42 having a cross-section similar in shape, but slightly smaller than the cross-section of central cavity 31 to permit the lower end 43 of bar 42 to be positioned in central cavity 31 (see also FIG. 1A). Bar 42 is also provided with a series of vertically aligned openings 44 extending through bar 42. As with bar 38 the height of support ring assembly 35 can be fixed at the desired height by inserting a locking pin 45 through on pair of aligned openings 32 and one of openings 44. In a more preferred embodiment the positioning of bar openings 44 and tubular member openings 32 are such that they are horizontally aligned with corresponding bar openings 32 and tubular member openings 27, respectively. This configuration facilitates assembly of device 1 and more achieves a more level positioning of support ring assembly 35.

Both anterior section 36 and posterior section 37 have a track 46 located on their upper surfaces 47 and 48, respectively. The purpose of track 46 is to provide a path of known position and dimensions along which rotational member 65 can slide. The cross-sectional configuration of track 46 can take any of the many known shapes that are known to serve the desired purpose. A particular cross-sectional configuration is illustrated in FIG. 7. In this configuration track 46 of anterior section 36 is an "L-shaped" channel 49 having its upper end 50 opening in upper surface 48. Posterior section 37 is provided with a similarly shaped channel 49. In an alternative embodiment illustrated in FIG. 7 recessed ball bearings 95 may be placed in channel 49 to decrease resistance of the sliding rotational member 65.

In a preferred embodiment both anterior section 36 and posterior section 37 will have alignment means located on the abutting ends of the two sections to facilitate proper joining and formation of a continuous circular track 46. One such alignment means can include pins 51 protruding from end surface 52 of anterior section 36 that can be extended into corresponding openings 53 in end surface 54 of posterior section 37. Openings 53 are shaped to permit pins 51 to extend completely into openings 53 but of a cross-sectional shape to permit a snug fit. Latches 55 and 56 are positioned on outer side wall 57 at the opposing end sections 58 and 59 of the posterior section 37 with catches 60 and 61 affixed on the outer side wall 62 at the opposing end sections 63 and 64 of anterior section 36.

As is illustrated in FIGS. 4-8, rotational member 65 includes a U-shaped tracking bar 66 with locking bars 67 and 68 extending from opposing ends 69 and 70, respectively, of tracking bar 66. Extending from the bottom surface 71 of tracking bar 66 is an L-shaped ridge 72 shaped and sized to fit in channel 49 to permit rotational member 65 to rotate when ridge 72 moves within channel 49. Each locking bar 67 and 68 is provided with a first series of openings 73 extending vertically through its respective bar and a second series of openings 74 extending horizontally through its respective bar.

To control the degree of rotation of tracking bar 66, posterior section 37 is provided with a series of horizontally extending openings 75 extending through channel 49 of section 37. These openings 75 are positioned at predetermined angles from the center of the circle formed by the joined sections 36 and 37. Pins 76 and 77 can be inserted through openings 75 to block channel 49 and thus limit the range of rotation that rotational member 65 can travel. In like fashion anterior section 36 can also be provided with a horizontal opening 75A extending through its channel 49A to restrict the travel of rotational member 65. In a preferred embodiment pins 76 and 77 are set to allow active rotational ranges of up to 60 degrees, up to 90 degrees, up to 120 degrees, up to 150 degrees, up to 180 degrees and up to 210 degrees. Numerous embodiments of the present invention are possible to allow multiple extensive ranges of horizontal rotation of the head without tilting. Thus, the present invention achieves the object of solving the cost effective need of a single device providing head and neck immobilization as well as furthering rehabilitation by safely strengthening muscles responsible for head rotation and increasing the range of said rotation.

Figure 9:
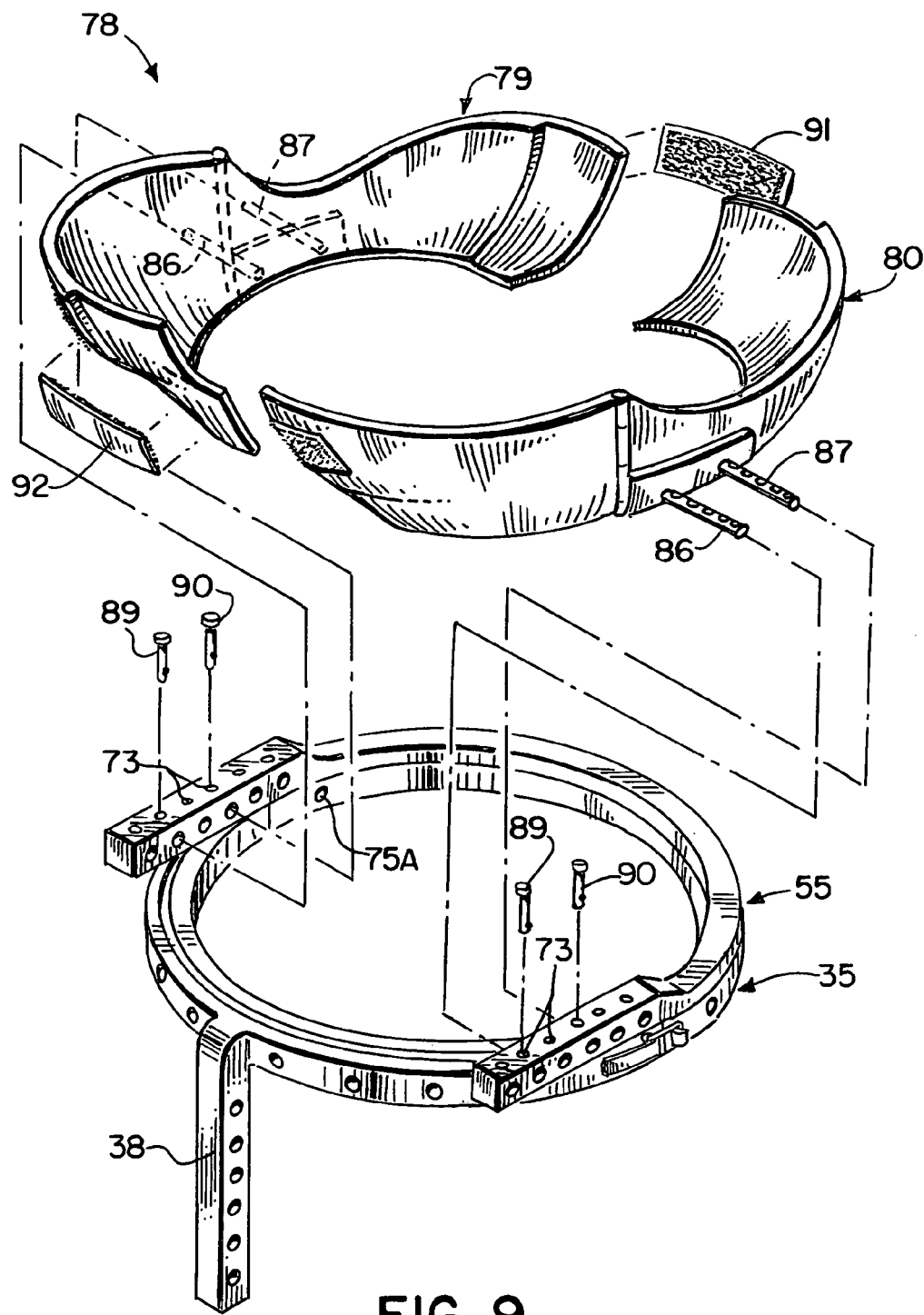
FIG. 9 is an exploded view illustrating the connectivity of left and right sections of the occipital-mandible support structure with the arcuate rotational member of the preferred embodiment of FIG. 1.
Figure 10:
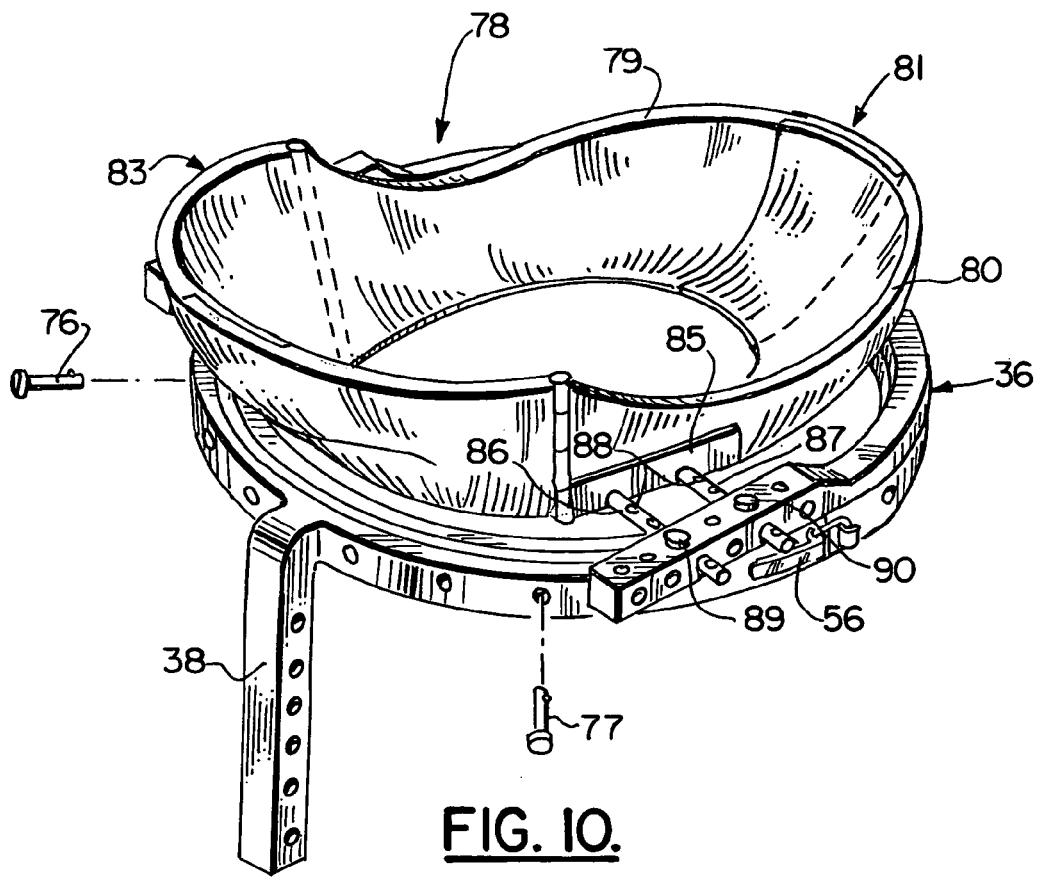
FIG. 10 is a three-quarter perspective view of the occipital-mandible support structure mounted on the rotational member of the preferred embodiment of FIG. 1.
Figure 11:
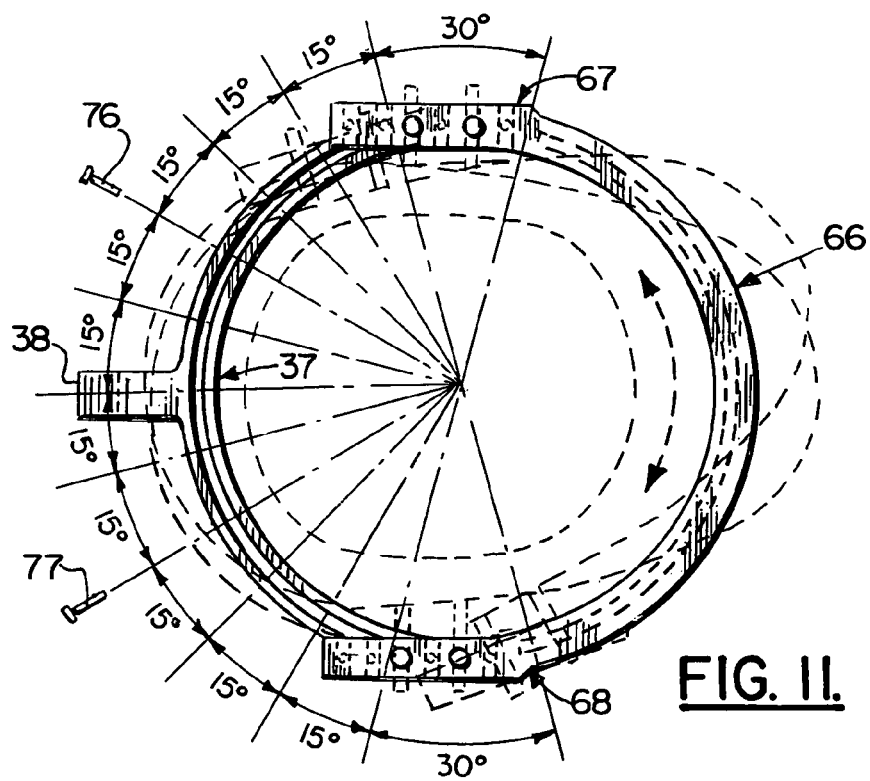
FIG. 11 is a top view of the rotational arc assembly of FIG. 1 indicating the rotational settings achievable by the preferred embodiment of FIG. 1.

As illustrated in FIGS. 9-10, the occipital-mandible support member 78 includes a left section 79 and a right section 80 preferably molded from a thermoset plastic or resin to form a rigid structure shaped to form a front cup-shaped section 81 in which the patient chin 82 can be positioned. Sections 79 and 80 when joined are also shaped to form a rear upward and outward curved section 83 that surrounds the upper back portion 84 of the patient neck and occipital portion 84A of the patient head. Each section 79 and 80 is provided with a rigid side plate 85 having pins 86 and 87 extending horizontally therefrom. Each pin 86 and 87 is provided with a series of vertically extending openings 88 that permit each locking pins 89 and 90 to be inserted through openings 88 and vertically extending openings 73 of locking bars 67 and 68, respectively.

Left and right sections 79 and 80 are attached to one another utilizing known attaching means such as hook and loop fasteners 91 and 92 or other known devices such as latches, cinches, snaps, etc. If desired, sections 79 and 80 can be constructed with hinges to facilitate donning and removal of the sections. In a more preferred embodiment, as illustrated in FIG. 4, left and right sections 79 and 80 will have inner cushioning pads 93 and 94, respectively, to prevent chaffing and provide comfort to the patient while wearing the device 1.

In rehabilitation of cervical or cervicothoracic spinal injuries, patients' treating physicians and physical therapists evaluate factors determining whether rotational range therapy is indicated; said factors include, but are not limited to type, location, and severity of the injury; stabilization of the spine, and range of motion without pain.

When rotational range therapy is indicated, patients' physician or physical therapist chooses the appropriate initial maximum degree of active rotation and schedule of progressive increases in maximum active rotation according to the needs of the individual patient. Factors to consider when increasing rotational range include, but are not limited to, range of motion without pain, stabilization of the spinal column and associated connective tissues, vertebral disc protrusion or herniation, nerve root impingement, and strength of the neck muscles. Physicians and physical therapists monitor said factors in treating patients with the present invention and method to increase cervical muscle strength and rotational range of the head. Between rotational therapy treatments to increase rotational range, the present invention is adjustable to a smaller rotational range functioning as a rotational range cervical brace to maintain gains in rotational range and further strengthen the cervical muscles.

Thus, the present invention achieves the object of facilitating a method of cervical therapy where the load of the head is transferred to the shoulders/upper chest and the head and neck actively rotate in progressively extensive ranges of horizontal rotation without tilting the head.

The present invention also functions as a rotational range cervical brace for patients with weakened neck muscles from neuromuscular diseases. The present invention comfortably supports the load of the head allowing patients to rotate their heads.

Once fitted to a patient, the present invention can be easily donned and removed in three assemblies. The present invention is removed by first releasing the hook and loop fastener 92 connecting the left occipital-mandible section 79 and right occipital-mandible section 80. The bilateral latches 55 and 56 connecting the anterior section 36 and posterior section 37 are then detached. The anterior section 36 and the adjoined rotational member 65 and occipital-mandible support member 78 are then pulled forward to separate from the posterior section 37. The bilateral hook and loop fasteners 17-20 connecting the rear neck plate 11 and the front neck-sternum plate 12 and are then detached to separate and remove the rear neck plate 11 and the front neck-sternum plate 12. Donning the present invention once fitted is achieved by simply reversing the removal steps.

These preferred embodiments, as well as other obvious alternative embodiments are to be included within the scope of the invention as defined by the following claims.

I claim:

1. A cervical brace and therapy device for use to rehabilitate an injured neck of a person comprising:
   a. a base support structure shaped to fit about the neck and rest on the shoulders of the person;
   b. a support ring assembly having a circular grooved track, said entire circular grooved track is configured to be receivable about and circumferentially surround a wearer's neck; the support ring assembly attachable to the base support structure in a horizontal position below the mandible of the person, the support ring assembly having an anterior section and a posterior section; the circular grooved track further having a series of horizontally extending openings spaced apart a known distance and extending through the circular grooved track; the circular grooved track further having at least two removable stop members extendable horizontally through the horizontally extending openings in the circular grooved track corresponding to a predetermined range of rotation, the stop removable members being variably positionable in the circular grooved track, c. a rotational curved member having a substantially half-circle shape, said entire rotational curved member is configured to partially surround a wearer's neck and is a member shaped to operatively and exactly mate with the circular grooved track of the support ring assembly in a manner to rotate about the circular grooved track; wherein each of the at least two removable stop members is affixable in at least two or more positions in the circular grooved track adapted to extend through one of said horizontally extending openings in the circular grooved track to limit the rotational curved range of the rotational member about the circular grooved track to a variably pre-determined rotational range;

d. an occipital-mandible support member shaped to accommodate the mandible and the occipital portions of the head of the person, the occipital-mandible support member being attachable to the rotational curved member in a manner to permit the occipital-mandible support member a predetermined range of rotation; and e. wherein the occipital-mandible support member is configured to provide a degree of motion of 0 degrees and 210 degrees, and at least one other mechanically restricted user-selectable degree of motion in-between.

2. A cervical brace and therapy device according to claim 1 wherein the base support structure comprises a rear neck contoured plate and a front contoured plate affixable to one another.

3. A cervical brace and therapy device according to claim 2 wherein at least one of the plates having openings to reduce the weight of the base support structure, better ventilate heat generated by the body positioned beneath the base support structure, and increase wearing comfort.

4. A cervical brace and therapy device according to claim 1 wherein the support ring assembly is attachable to the base support structure at two or more places.

5. A cervical brace and therapy device according to claim 1 wherein the base support structure comprises a neck-sternum section having edges and a neck-upper back section having edges, said neck-sternum section and said neck-upper back section are attachable to one another along their edges by a securing means and shaped when joined to rest on the upper back, shoulders and sternum of the person.

6. A cervical brace and therapy device according to claim 5 wherein the securing means is selected from a group consisting of a hook and loop fastener, latches, snaps, cinches, or a combination thereof.

7. A cervical brace and therapy device according to claim 5 wherein the edges are constructed to mate in a tongue-and-groove or overlapping manner.

8. A cervical brace and therapy device according to claim 5 wherein the neck-sternum section and the neck-upper back section each have a rigid outer shell and a cushioning inner liner positioned to contact the person.

9. A cervical brace and therapy device according to claim 8 wherein the liner is attachable by one or more hook and loop fasteners.

10. A cervical brace and therapy device according to claim 5 wherein the neck-upper back section further comprises a first vertically extending hollow tubular member for receiving one end of a first vertical positioning shaft extending vertically downward from the posterior section of the support ring assembly.

11. A cervical brace and therapy device according to claim 10 wherein the first vertically extending hollow tubular member and the first vertical positioning shaft are each provided with a series of opening extending there through sized and positioned to permit the insertion of a locking pin through aligned openings of the first vertically extending hollow tubular member and the first vertical positioning shaft.

12. A cervical brace and therapy device according to claim 11 wherein the cross-sectional shape of the first vertically extending hollow tubular member is shaped having two or more sides and the cross-sectional shape of the first vertical positioning shaft is of similar smaller shape to permit the first vertical positioning shaft to extend into the first vertically extending hollow tubular member.

13. A cervical brace and therapy device according to claim 10 wherein the neck-sternum section further comprises a second vertical extending hollow tubular member for receiving one end of a second vertical positioning shaft extending vertically downward from the anterior section of the support ring assembly.

14. A cervical brace and therapy device according to claim 13 wherein the second vertically extending hollow tubular member and the second vertical positioning shaft are each provided with a series of opening extending there through sized and positioned to permit the insertion of a locking pin through aligned openings of the second vertically extending hollow tubular member and the second vertical positioning shaft.

15. A cervical brace and therapy device according to claim 1 wherein the anterior section and the posterior section of the support ring assembly are affixable to one another to form a ring sized to fit about the neck of the person.

16. A cervical brace and therapy device for use to rehabilitate an injured neck of a person comprising:

a. a base support structure shaped to fit about the neck and rest on the shoulders of the person; the base support structure comprising a neck-sternum section having edges and a neck-upper back section having edges, said neck-sternum section and said neck-upper back section are attachable to one another along their edges by a securing means and shaped when joined to rest on the upper back, shoulders and sternum of the person; wherein the neck-sternum section further comprises a first vertical extending hollow tubular member for receiving one end of a first vertical positioning shaft extending vertically downward from the anterior section of a support ring assembly; the first vertically extending hollow tubular member and the first vertical positioning shaft are each provided with a series of openings extending there through sized and positioned to permit the insertion of a locking pin through aligned openings of the first vertically extending hollow tubular members and the first vertical positioning shaft;

b. said support ring assembly having a circular grooved track and attachable to the base support structure in a horizontal position below the mandible of the person, the support ring assembly having an anterior section and a posterior section; the posterior section of the support ring assembly having a series of horizontally extending openings spaced apart a known distance and extending through the circular grooved track;

c. a rotational curved member having opposing ends and attached to the support ring assembly in a manner to rotate about the support ring assembly; each of the opposing ends of the rotational curved member are provided with a first series of vertically extending openings extending through the rotational curved member and a second series of horizontally extending openings extending through the rotational member;

d. an occipital-mandible support member shaped to accommodate the mandible and the occipital portions of the head of the person, the occipital-mandible support member being attachable to the rotational curved member in a manner to permit the occipital-mandible support member a predetermined range of motion; and wherein the occipital-mandible support member is configured to provide a degree of motion of between about 0 degrees and 210 degrees, and at least one other user-selectable degree of motion in-between; the occipital-mandible support member having opposing pairs of horizontally extending pins sized and positioned to extend through corresponding openings of the second series of horizontally extending openings of the rotational curved member, the horizontally extending pins having a series of vertically extending openings extending therethrough; a first set of locking pins each extendable through the aligned openings formed by one of the vertically extending openings in the horizontally extending pin and one of the first series of the vertically extending openings in the rotational curved member; and a second set of removable locking pins extendable through the horizontally extending openings in the posterior section of the support ring assembly corresponding to a predetermined range of rotation.

17. A cervical brace and therapy device according to claim 1 wherein the occipital-mandible support member is comprised of a left section and a right section affixed to one another by an attachment means.

18. A cervical brace and therapy device according to claim 17 wherein the attachment means is selected from a group consisting of hook and loop fasteners, latches, snaps, cinches, or a combination thereof.

19. A cervical brace and therapy device according to claim 17 wherein the left section and the right section each have a rigid outer shell having an attachable cushioning inner liner positioned to contact the mandible and occipital region of the person when used.

20. A structure for use with a cervical brace and therapy device to control the degree of active head rotation without permitting the tilting of the head the improvement to which comprising:

a. a support ring assembly having an anterior section, a posterior section, and a circular grooved track, said entire circular grooved track is configured to be receivable about and circumferentially surround a wearer's neck, the circular grooved track assembly further having a series of horizontally extending openings spaced apart a known distance and extending through the circular grooved track; the circular grooved track further having two or more removable stop members extendable horizontally through the horizontally extending openings in the circular grooved track corresponding to a predetermined range of rotation; the stop members being variably positionable in the circular grooved track to variably restrict a range of rotation of the rotational curved member about the circular grooved track to a predetermined range of rotation, b. the rotational curved member having a substantially half-circle shape and opposing ends, said entire rotational curved member is configured to partially surround a wearer's neck and is shaped to operatively and exactly mate with the circular grooved track of the support ring assembly in a manner to permit the rotational curved member to rotate about the circular grooved track within a predetermined range of rotation; wherein each of the removable stop members is affixable in at least two or more positions in the circular grooved track and adapted to extend through one of said horizontally extending openings in the circular grooved track to limit the rotational range of the rotational curved member about the circular grooved track to a variably pre-determined rotational range; and c. an occipital-mandible support member shaped to accommodate the mandible and the occipital portions of the head of the person, the occipital-mandible support member being attachable to the rotational curved member in a manner to permit the occipital-mandible support member the predetermined range of rotation; and d. wherein the occipital-mandible support member is configured to provide the predetermined range of rotation of between about 0 degrees and 210 degrees determined by the position of the stop members.

21. A structure according to claim 20 wherein the anterior section and the posterior section of the support ring assembly are attachable to one another to form a ring sized to fit about the neck of the person.

22. A structure according to claim 21 wherein:

a. each of the opposing ends of the rotational curved member are provided with a first series of vertically extending openings extending through the rotational curved member and a second series of horizontally extending openings extending through the rotational curved member;

b. the occipital-mandible support member having opposing pairs of horizontally extending pins sized and positioned to extend through corresponding openings in the second series of horizontally extending openings of the rotational curved member, the horizontally extending pins having a series of vertically extending openings extending therethrough;

c. the posterior section of the support ring assembly having the series of horizontally extending openings spaced apart a known distance and extending through the circular track grooved;

d. a first set of locking pins extendable through aligned openings formed by one of the vertically extending openings in the horizontally extending pin and one of the vertically extending openings in the rotational curved member.

23. A method of cervical therapy on a person having a head, back side of a lower neck, an upper back, a lower throat, an upper chest and shoulders that transfers the load of the patient head to the patient shoulders while permitting a limited range of horizontal head rotation, which method comprises:

(a) providing a base support structure shaped to fit about the neck and rest on the shoulders of the person;

(b) providing a support ring assembly having a circular grooved track, said entire circular grooved track is configured to be receivable about and circumferentially surround a wearer's neck; the support ring assembly attachable to the base support structure in a horizontal position below the mandible of the person, the support ring assembly having an anterior section and a posterior section; the circular grooved tracked further having a series of horizontally extending openings spaced apart a known distance and extending through the circular grooved track; the circular grooved track further having at least two removable stop members extendable horizontally through the horizontally extending openings in the circular grooved track corresponding to a predetermined range of rotation, the removable stop members being variably positionable in the circular track;

(c) providing a rotational curved member having a substantially half-circle shape, said entire rotational curved member is configured to partially surround a wearer's neck and is shaped to operatively and exactly mate with the circular grooved track of the support ring assembly in a manner to rotate about the circular grooved track; wherein each of the at least two removable stop members is affixable in at least two or more positions in the circular track adapted to extend through one of said horizontally extending openings in the circular grooved track to limit the rotational range of the rotational curved member about the circular grooved track to a variably pre-determined rotational range;

(d) providing an occipital-mandible support member shaped to accommodate the mandible and the occipital portions of the head of the person, the occipital-mandible support member being attachable to the rotational curved member in a manner to permit the occipital-mandible support member a predetermined range of rotation; wherein the occipital-mandible support member is configured to provide a degree of motion of between 0 degree and 210 degrees, and at least one other mechanically restricted user-selectable degree of motion in-between;

(e) positioning the base support structure on the shoulders of the person;

(f) affixing the support ring assembly and the rotational curved member to the base support member at a position below the patient mandible;

(g) affixing the occipital-mandible support member to the rotational curved member and about the patient occipital and mandible at a position that supports the patient head at a desired horizontal position;

(h) positioning the removable stop members in the circular grooved track and selectively limiting the determined rotational motion of about 0 degree and 210 degrees of the rotational curved member relative to the circular grooved track.

(i) allowing the patient head to rotate within the predetermined rotational range of head movement for a desired period of time.

24. A method according to claim 23 further comprising:

a. adjusting the position of the stop members in the circular grooved track to permit a second predetermined range of horizontal head rotation; and b. allowing the patient head to rotate within the predetermined second range of head movement.

25. A method according to claim 23 further comprising periodic adjusting of the movable stop members to permit increasingly greater range of head rotation.

26. A method according to claim 23 further comprising the step of positioning the base support structure on the back side of the patient lower neck, the patient upper back, the patient lower throat, the patient upper chest, and the patient shoulder in a manner to permit the base support structure to transfer the load of the patient head to the patient shoulders.

* * * * *